(12) United States Patent
Thomas (10) Patent No.: US 10,758,168 B2
(45) Date of Patent: Sep. 1, 2020

(54) METHOD AND SYSTEM FOR THE AUTOMATED ASSESSMENT OF FATIGUE MITIGATION STRATEGIES

(75) Inventor: Lisa C. Thomas, Kirkland, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 13/525,954

(22) Filed: Jun. 18, 2012

(65) Prior Publication Data
US 2013/0338445 A1     Dec. 19, 2013

(51) Int. Cl.
*A61B 5/18*     (2006.01)

(52) U.S. Cl.
CPC ..................... *A61B 5/18* (2013.01)

(58) Field of Classification Search
CPC .................................................. G06F 19/3418
USPC .................................................. 600/545, 300
See application file for complete search history.

(56) References Cited

U.S. PATENT DOCUMENTS

| | | | |
|---|---|---|---|
| 5,732,696 A * | 3/1998 | Rapoport et al. | 600/301 |
| 6,167,298 A * | 12/2000 | Levin | 600/545 |
| 7,192,401 B2 * | 3/2007 | Saalasti et al. | 600/500 |
| 7,450,016 B2 | 11/2008 | Isaji et al. | |
| 7,969,327 B2 | 6/2011 | Christophe et al. | |
| 8,022,831 B1 | 9/2011 | Wood-Eyre | |
| 8,075,484 B2 | 12/2011 | Moore-Ede | |
| 2004/0201481 A1 * | 10/2004 | Yoshinori | B60H 1/00 340/575 |
| 2004/0243013 A1 * | 12/2004 | Kawachi | A61B 5/18 600/509 |
| 2005/0059870 A1 * | 3/2005 | Aceti | A61B 5/0002 600/340 |

(Continued)

FOREIGN PATENT DOCUMENTS

| | | |
|---|---|---|
| EP | 2 434 465 A2 | 3/2012 |
| GB | 2 390 460 A | 7/2004 |

(Continued)

OTHER PUBLICATIONS

Burton et al., "Physiological effects of exercise", British Journal of Anaestheia, 2004 4(6): 185-188.*

(Continued)

*Primary Examiner* — Gary Jackson
*Assistant Examiner* — Sebastian X Lukjan
(74) *Attorney, Agent, or Firm* — Alston & Bird LLP (57) ABSTRACT

A method, system, and computer program product are provided to automatically assess a plurality of fatigue mitigation strategies. In the context of a method, fatigue information is received for a subject and determination is made as to whether the subject is fatigued. In an instance in which the subject is fatigued, the method determines an estimated effectiveness of each of a plurality of fatigue mitigation strategies based upon fatigue information for the subject and one or more constraints and characteristics of a respective fatigue mitigation strategy. The determination of the estimated effectiveness of each of the plurality of fatigue mitigation strategies may also be based upon at least one of a time to become effective, a duration of the effectiveness and a side effect. The method also identifies at least one fatigue mitigation strategy to address fatigue of the subject.

20 Claims, 5 Drawing Sheets

Pilot Inputs

| 60, M, Weight=Normal, No known sleep problems, No medications, 100 mg caffeine at 8 am, Sandwich + apple at 11 am | Last Sleep: 2400-0600, low qual Duty shift: 0700-1600 Current Time = 1400 Time Zone change = 0 hrs in past 48 hrs, 0 hrs expected | Time awake: 8 hrs Time on shift: 7 hrs Time til next sleep op = 6 hrs Current flight phase: Cruise, normal ops, low workload Time til landing: <1 hr |
|---|---|---|

Mitigation Strategies

| Napping | Caffeine | Water/Hydration |
|---|---|---|
| •Workload must be low<br>•Flight phase must be Cruise<br>•Circ Phase must be near trough<br>•*Time til landing must be >2 hrs*<br>•*Suggested length of nap = 20-40 min*<br>•*Side effect: Risk of sleep inertia* | •Pilot must have no caffeine intolerance/contraindication<br>•*Time til next sleep op > 4 hrs for 100 mg dose, >8 hrs for 200 mg dose*<br>•*Time til effectiveness = 30 min; time til landing must be > 45 min*<br>•*Side effect(s): dehydration, disrupted or delayed sleep at next sleep op* | •Time til landing must be >30 min (to allow lav time)<br>•Time til effectiveness = x min<br>•*Note limited effectiveness for severe fatigue effects* |

(56) References Cited

U.S. PATENT DOCUMENTS

| | | | |
|---|---|---|---|
| 2007/0167847 A1* | 7/2007 | Guglielmino | A61B 5/02438 600/509 |
| 2008/0122636 A1* | 5/2008 | Matos | 340/576 |
| 2010/0009326 A1* | 1/2010 | Mori | A61B 5/165 434/236 |
| 2010/0214105 A1 | 8/2010 | Manotas | |
| 2012/0078122 A1* | 3/2012 | Yokoyama | A61B 5/0245 600/484 |
| 2012/0112879 A1* | 5/2012 | Ekchian | A61B 5/117 340/5.53 |
| 2012/0143019 A1* | 6/2012 | Russell | A61B 5/0205 600/301 |

FOREIGN PATENT DOCUMENTS

| | | |
|---|---|---|
| JP | 2007 114170 A | 5/2007 |
| WO | WO 2008/091965 | 7/2008 |
| WO | WO 2009052633 A1 * | 4/2009 |

OTHER PUBLICATIONS

General Recommendations on Fatigue Risk Management for the Canadian Forces, Defence R&D Canada Technical Report DRDC Toronto TR 2010-056, Apr. 2010, 84 pages.

Fatigue Risk Management Systems Implementation Guide for Operations, ICAO publication: Jul. 2011, 150 pages.

Review of Fatigue Detection and Prediction Technologies, National Road Transport Commission Report ISBN: 0 642 54469,Sep. 7, 2000, 41 pages.

Search Report for Great Britain Application No. GB 1310167.0 dated Dec. 9, 2013.

Office Action for Great Britain Application No. 1310167.0 dated Feb. 28, 2017, 7 pages.

Hockey, G. Robert et al.; "Effects of Negative Mood States on Risk in Everyday Decision Making"; Cognition and Emotion, 2000, 14 (6), 823-855.

Examination Report for Great Britain Application No. GB1310167.0 dated Sep. 8, 2017, 3 pages.

* cited by examiner

Pilot Inputs

[Box 1]
Time awake: 8 hrs
Time on shift: 7 hrs
Time til next sleep op = 6 hrs
Current flight phase: Cruise, normal ops, low workload
Time til landing: <1 hr

[Box 2]
Last Sleep: 2400-0600, low qual
Duty shift: 0700-1600
Current Time = 1400
Time Zone change = 0 hrs in past 48 hrs, 0 hrs expected

[Box 3]
60, M, Weight=Normal,
No known sleep problems,
No medications,
100 mg caffeine at 8 am,
Sandwich + apple at 11 am

Mitigation Strategies

Water/Hydration
- Time til landing must be >30 min (to allow lav time)
- Time til effectiveness = x min
- *Note limited effectiveness for severe fatigue effects*

Caffeine
- Pilot must have no caffeine intolerance/contraindication
- Time til next sleep op > 4 hrs for 100 mg dose, >8 hrs for 200 mg dose
- Time til effectiveness = 30 min; time til landing must be > 45 min
- *Side effect(s): dehydration, disrupted or delayed sleep at next sleep op*

Napping
- Workload must be low
- Flight phase must be Cruise
- Circ Phase must be near trough
- *Time til landing must be >2 hrs*
- Suggested length of nap = 20-40 min
- *Side effect: Risk of sleep inertia*

Recommendations at this time:

1) Caffeine: Effectiveness level = HIGH
   Take one of the following
   - Soda (35 mg per 12 oz can)
   - Tea (30 mg per 6 oz)
   - Coffee (~100 mg per 8 oz)
   - ½ caffeine pill (100 mg)
   - 1 stick caffeinated gum (50 mg)

NOTES: Do not exceed 100 mg caffeine at this time, or future sleep may be disrupted or delayed. Expect 30 min until full effectiveness. Expect up to 4 hours of effectiveness (for 100 mg, lower time for lower doses).

2) Water: Effectiveness level = LOW
   Take the following
   - 1 8oz glass of water now
   - 1 8oz glass of water in 30 minutes NOTES: Water is intended to reduce dehydration, a side effect of caffeine which can increase fatigue.
   Expect increased lav breaks; plan accordingly.

DO NOT USE at this time:

1) Napping. Expected workload and time until landing do not permit sufficient time for napping and recovery from post-nap sleep inertia.

2) Light therapy. Exposure to bright light at this time will not produce effective fatigue reduction and may disrupt or delay sleep at the next sleep opportunity.

DO NOT USE

FIG. 5

METHOD AND SYSTEM FOR THE AUTOMATED ASSESSMENT OF FATIGUE MITIGATION STRATEGIES

TECHNOLOGICAL FIELD

An example embodiment of the present disclosure relates generally to the detection of fatigue in a subject and, more particularly, to the automated assessment of a plurality of fatigue mitigation strategies.

BACKGROUND

Fatigue is a common issue in a variety of contexts. Although people may know in general of the issues that may be created by fatigue, individuals oftentimes fail to recognize debilitating fatigue in themselves as evidenced, for example, by the number of motor vehicle accidents that involve drowsy drivers. Additionally, fatigue has been determined to reduce decision-making capabilities by reducing the set of options that are considered and/or by reducing the effort undertaken to analyze a situation and to make an effective decision. In other words, people who are fatigued may tend to go with an easy solution to a situation because they do not wish to make the effort required to consider all of the options or they may not recall that several alternatives exist.

Notwithstanding the risks posed by fatigue, the advice given to people who are fatigued or may become fatigued is generally relatively vague and in not individually tailored for an individual or the particular circumstances that currently confront the individual. For example, an individual may simply be advised to get a good night's sleep, eat a healthy diet or take a nap when the individual feels tired. In some circumstances, one or all of these forms of general advice may be inappropriate or inapplicable. For example, napping is commonly touted to reduce both fatigue and sleepiness. However, napping has a number of drawbacks that may make it difficult for an individual to implement in a number of circumstances, although it is left to the individual to determine how to apply, if at all, the generalized advice of napping to reduce fatigue.

BRIEF SUMMARY

A method, system, and computer program product are provided according to an example embodiment in order to automatically assess a plurality of fatigue mitigation strategies. As such, the method, system, and computer program product of an example embodiment may identify one or more fatigue mitigation strategies that are tailored for the subject and the circumstances that currently confront the subject. Thus, the method, system, and computer program product of an example embodiment may reduce the issues associated with fatigue by providing advice regarding a fatigue mitigation strategy to a subject who may be suffering from fatigue in a manner that is relevant and useful to the subject, thereby increasing the likelihood that the subject may avail themselves of the fatigue mitigation strategy that is suggested and may, in turn, become less fatigued.

In one embodiment, a method for the automated assessment of a plurality of fatigue mitigation strategies is provided. The method of this embodiment receives fatigue information for a subject and determines if the subject is fatigued. In an instance in which the subject is fatigued, the method determines, with processing circuitry, an estimated effectiveness of each of a plurality of fatigue mitigation strategies based upon fatigue information for the subject and one or more constraints and characteristics of a respective fatigue mitigation strategy. In one embodiment, the determination of the estimated effectiveness of each of the plurality of fatigue mitigation strategies is also based upon at least one of a time to become effective, a duration of the effectiveness and a side effect. The method also identifies at least one fatigue mitigation strategy to address fatigue of the subject and, in one embodiment, may order the plurality of fatigue mitigation strategies based upon the estimated effectiveness. In one embodiment, the method also identifies at least one fatigue mitigation strategy that is not recommended for the subject.

In regards to the receipt of the fatigue information for the subject, state information relating to fatigue of the subject or efficacy of one or more of the mitigation strategies may be received. Additionally or alternatively, the receipt of fatigue information for the subject may include receiving information from one or more fatigue detection devices including one or more fatigue effects of the subject. In this embodiment, the method may also include determining the strength of the one or more fatigue effects. The method of one embodiment may also include weighting the fatigue information based upon a value of the fatigue information to the determination of the estimated effectiveness of the fatigue mitigation strategies. In this embodiment, the determination of the estimated effectiveness of each of the plurality of fatigue mitigation strategies may include excluding one or more fatigue mitigation strategies that are in conflict with highly weighted fatigue information.

In another embodiment, a system for the automated assessment of a plurality of fatigue mitigation strategies is provided. The system includes processing circuitry configured to receive fatigue information for a subject and to determine if the subject is fatigued. In an instance in which the subject is fatigued, the processing circuitry is configured to determine an estimated effectiveness of each of a plurality of fatigue mitigation strategies based upon the fatigue information of the subject and one or more constraints and characteristics of a respective fatigue mitigation strategy. In one embodiment, the processing circuitry is configured to determine the estimated effectiveness of each of the plurality of fatigue mitigation strategies based also upon at least one of a time to become effective, a duration of the effectiveness and a side effect. The processing circuitry is also configured to identify at least one fatigue mitigation strategy to address fatigue of the subject and, in one embodiment, is configured to order the plurality of fatigue mitigation strategies based upon the estimated effectiveness. Further, the processing circuitry of one embodiment may be further configured to also identify at least one fatigue mitigation strategy that is not recommended for the subject.

In regards to the receipt of the fatigue information of a subject, the processing circuitry of one embodiment may be configured to receive state information relating to fatigue of the subject or efficacy of one or more of the mitigation strategies. Additionally or alternatively, the processing circuitry may be configured to receive fatigue information for the subject by receiving information from one or more fatigue detection devices regarding one or more fatigue effects of the subject. The processing circuitry of this embodiment may be further configured to determine the strength of the one or more fatigue effects. The processing circuitry of one embodiment may also be configured to weight the fatigue information based upon a value of the fatigue information to the determination of the estimated effectiveness of the fatigue mitigation strategies. In this regard, the processing circuitry may be configured to determine the estimated effectiveness of each of the plurality of fatigue mitigation strategies by excluding one or more fatigue mitigation strategies that are in conflict with highly weighted fatigue information.

In a further embodiment, a computer program product is provided to automatically assess a plurality of fatigue mitigation strategies. The computer program product includes a non-transitory computer-readable storage medium having computer-readable program code stored therein that in response to execution by processing circuitry cause an apparatus to at least receive fatigue information for a subject and determine if the subject is fatigued. In an instance in which the subject is fatigued, the computer-readable program code, upon execution by the processing circuitry, may also cause the apparatus to determine an estimated effectiveness of each of a plurality of fatigue mitigation strategies based upon the fatigue information for the subject and one or more constraints and characteristics of a respective fatigue mitigation strategy. The computer-readable program code of this embodiment, upon execution by the processing circuitry, also causes the apparatus to identify at least one fatigue mitigation strategy to reduce fatigue of the subject. The computer-readable code of one embodiment, in response to execution by the processing circuitry, may further cause the apparatus to identify at least one fatigue mitigation strategy that is not recommended for the subject.

BRIEF DESCRIPTION OF THE DRAWINGS

Having thus described example embodiments of the present disclosure in general terms, reference will now be made to the accompanying drawings, which are not necessarily drawn to scale, and wherein:

DETAILED DESCRIPTION

The present disclosure now will be described more fully hereinafter with reference to the accompanying drawings, in which some, but not all embodiments are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

A method, system and computer program product are provided for the automated assessment of a plurality of fatigue mitigation strategies. By assessing a plurality of fatigue mitigation strategies based upon fatigue information for a particular subject, one or more fatigue mitigation strategies that are most appropriate to address the fatigue of the subject may be identified. Thus, the fatigue mitigation strategy that is suggested to the subject is tailored for the subject and for the situation that currently confronts the subject. Thus, a subject may implement at least one of the recommended fatigue mitigation strategies so as to avoid at least some of the deleterious effects of fatigue.

As an initial matter, the method of an example embodiment may receive fatigue information for a subject. The fatigue information may relate to a variety of different types of subjects, such as pilots, drivers, train operators, operators of other types of equipment or machinery or the like. As shown in block 20 of FIG. 1, the fatigue information as received may include state information relating to the fatigue of the subject or the efficacy of one or more mitigation strategies. Indeed, the state information may include information relating to factors that contribute to or affect the severity of fatigue effects, sleep deprivation and/or sleep inertia. Additionally or alternatively, the state information may relate to factors that affect the efficacy of a mitigation strategy, as discussed below.

In an example embodiment in which the subject is a pilot, the state information may include demographic information, such as age, gender, time and date of the last meal, the general health of the subject, the level of activity being performed by the subject and the like. The state information may also include information regarding the environment or other circumstances describing the current context in which the subject is deployed. For example, the state information may include the number of hours that the subject has been on duty, the work shift of the subject, the work load of the subject, the phase of the flight, e.g., takeoff, cruising at altitude, landing, etc., the hours that remain until the next opportunity for the subject to rest, etc. Another example of the state information relating to the fatigue of the subject are factors relating to the physiological state of the subject including the circadian phase of the subject, the time of day, whether the subject is experiencing jet lag that is, a mismatch between the circadian phase of the subject and the actual time of day, the time since the subject last slept and the quality of the last sleep. Further, the state information relating to the efficacy of one or more mitigation strategies may include the weight of a subject, known sleep problems of the subject, medications taken by the subject, caffeine ingested by the subject, contraindications, that is, circumstances that may not allow the particular mitigation strategy, e.g., the inability of a subject to take caffeine, etc.

Figure 1:
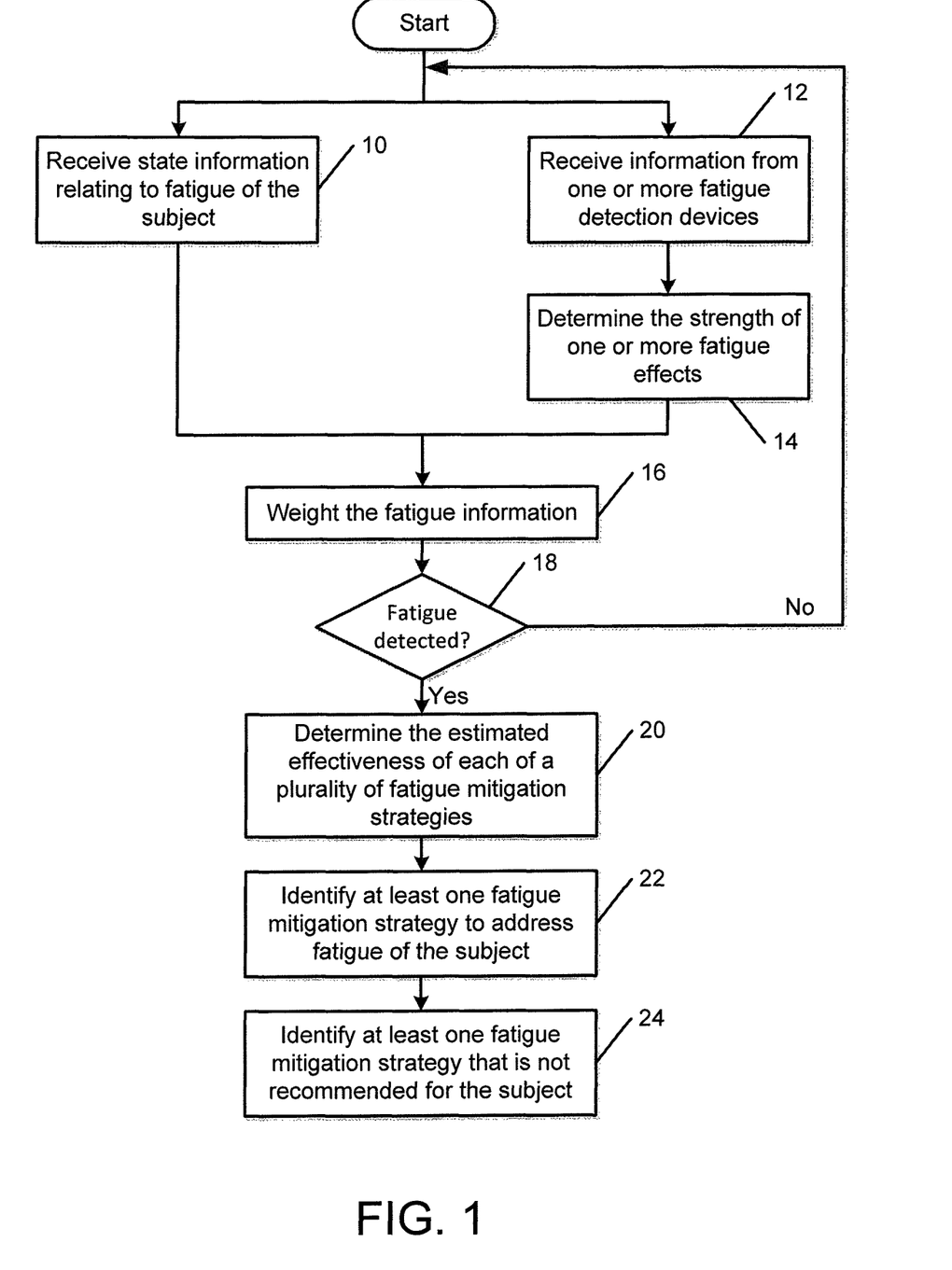
FIG. 1 is a block diagram of the operations performed in accordance with an example embodiment of the present disclosure.
Figure 2:
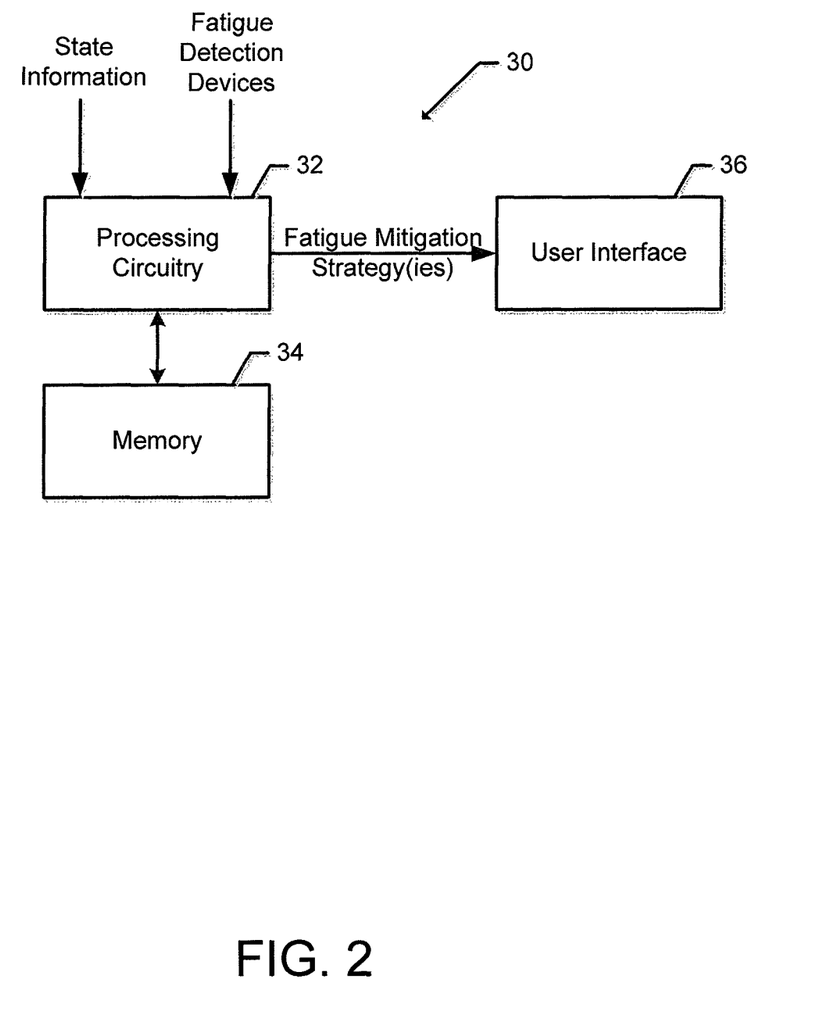
FIG. 2 is a block diagram of an apparatus that may be specifically configured in accordance with an example embodiment of the present disclosure.

The operations depicted by FIG. 1 including the receipt of fatigue information for a subject and, more particularly, the receipt of state information relating to fatigue of the subject may be performed by a system 30, such as shown in FIG. 2, that may be specifically configured to perform the operations. In this regard, the system 30 may include processing circuitry 32 and a memory device 34 that may cooperate in order to control the various functions described herein. The processing circuitry 32 may, for example, be embodied as various means including one or more microprocessors, one or more coprocessors, one or more multi-core processors, one or more controllers, one or more computers, various other processing elements including integrated circuits such as, for example, an ASIC (application specific integrated circuit) or FPGA (field programmable gate array), or some combination thereof. In some example embodiments, the processing circuitry 32 is configured to execute instructions stored in the memory device 34 or otherwise accessible to the processing circuitry. These instructions, when executed by the processing circuitry 32, may cause the system 30 to perform one or more of the functionalities described herein. As such, whether configured by hardware or software methods, or by a combination thereof, the processing circuitry 32 may comprise an entity capable of performing operations according to embodiments of the present disclosure while configured accordingly. Thus, for example, when the processing circuitry 32 is embodied as an ASIC, FPGA or the like, the processing circuitry may comprise specifically configured hardware for conducting one or more operations described herein. Alternatively, as another example, when the processing circuitry 32 is embodied as an executor of instructions, such as may be stored in the memory device 34, the instructions may specifically configure the processing circuitry to perform one or more algorithms and operations described herein.

The memory device 34 may include, for example, volatile and/or non-volatile memory. The memory device 34 may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory device 34 may comprise any non-transitory computer readable storage medium. The memory device 34 may be configured to store information, data, applications, instructions, or the like for enabling the system 30 to carry out various functions in accordance with example embodiments of the present disclosure. For example, in some example embodiments, the memory device 34 is configured to store program instructions for execution by the processing circuitry 32.

The system 30 of FIG. 2 also includes a user interface 36 in communication with the processing circuitry 32 to provide information to a subject regarding one or more fatigue mitigation strategies that are recommended for the subject. In one embodiment, the user interface 36 may include, for example, a keyboard and/or a touch sensitive display, for receiving user input. The user interface 36 may also include a display for presenting information to a subject regarding one or more fatigue mitigation strategies.

As shown in block 10 of FIG. 1, the system 30, such as the processing circuitry 32, may be configured to receive the fatigue information for a subject, including the state information relating to the fatigue of the subject. Additionally or alternatively, the system 30, such as the processing circuitry 32, may be configured to receive other types of fatigue information for the subject including, for example, information from one or more fatigue detection devices regarding one or more fatigue effects of the subject. See block 12. Although various types of fatigue detection devices may provide information regarding fatigue effects of the subject, a fatigue detection device that is configured to track the subject's eye movements may be configured to provide information regarding the eye movements to the system 30, such as the processing circuitry 32. In this regard, consistent eye movements may be indicative of an alert subject, while a reduction in eye movements may be indicative of a fatigued subject. Additionally or alternatively, a fatigue detection device may be configured to analyze the voice of the subject and to provide information regarding the voice of the subject to the system 30, such as the processing circuitry 32. In this regard, a voice that is lower than normal may be indicative of a fatigued subject. In one embodiment, a fatigue detection device may be configured to detect closure of the subject's eyes and to provide information regarding eye closure to the system 30, such as the processing circuitry 32. In this regard, increased eye closure may be indicative of a fatigued subject. Additionally or alternatively, a fatigue detection device may be configured to detect nodding of the subject's head and to provide information regarding head nodding to the system 30, such as the processing circuitry 32. In this regard, head nodding may be indicative of a fatigued subject. In one embodiment, a fatigue detection device may be configured to detect posture changes of the subject and to provide information regarding the posture changes to the system 30, such as the processing circuitry 32. In this regard, a change in the quality of the posture may be indicative of a fatigued subject.

Regardless of the type of information collected by one or more fatigue detection devices, the fatigue detection devices may be configured to repeatedly monitor the subject for one or more fatigue effects that may be an accurate predictor of fatigue. Similarly, the system 30 may be configured to repeatedly receive other types of fatigue information including state information for the subject so as to permit the fatigue level of the subject to be repeatedly determined.

In one embodiment, the system 30, such as the processing circuitry 32, may be configured to determine the strength of the one or more fatigue effects about which the one or more fatigue detection devices provided information. See block 14. In this regard, based upon, for example, the eye movements of the subject, the pitch of the subject's voice, the percent of time that the subject's eyes are closed, the frequency with which the subject's head nods, the type of posture changes or the like, the system 30, such as the processing circuitry 32, may determine the strength of each fatigue effect. For example, greater strengths may be associated with fatigue effects that represent stronger or more pronounced effects of fatigue and lower strengths being associated with fatigue effects that are indicative of fatigue that has been detected in an early stage. In one embodiment, one or more predefined thresholds may be established for each of the different types of fatigue information provided by the fatigue detection devices with the predefined thresholds defining the ranges of each type of fatigue information that are associated with a strongly fatigued state, a moderately fatigued state and a minimally fatigued state.

In one embodiment, the system 30, such as the processing circuitry 32, may be configured to weight the fatigue information based upon a value of the fatigue information to the determination of the estimated effectiveness of the fatigue mitigation strategies. See block 16 of FIG. 1. In this regard, those types of fatigue information that are more valuable to the determination of the estimated effectiveness of the fatigue mitigation strategies may be weighted more greatly than other types of fatigue information that are of less value to the determination of the estimated effectiveness of the fatigue mitigation strategies. By way of example, gender has a significant, but small effect on fatigue, while age has a larger effect on fatigue. Thus, the fatigue information associated with the age of the subject may be weighted more greatly than the fatigue information associated with the gender of the subject. Additionally or alternatively, the fatigue information provided by fatigue detection devices may be weighted in accordance with the strength of the fatigue effects represented by the fatigue information with fatigue information representative of a stronger fatigue effect being more greatly weighted than fatigue information representative of a weaker fatigue effect.

The system 30, such as the processing circuitry 32, may then determine if the subject is fatigued based upon an analysis of the fatigue information that has been received. See block 18 of FIG. 1. Although fatigue may be determined in various manners, the system 30, such as the processing circuitry 32, of one embodiment may determine if the subject is fatigued based upon an analysis of the fatigue information, such as the weighted fatigue information. In one embodiment, the system 30, such as a processing circuitry 32, may include one or more predefined combinations of fatigue information, such as weighted fatigue information, that are indicative of the subject being fatigued. In this embodiment, in an instance in which the fatigue information satisfies at least one of the predefined combinations, the system 30, such as the processing circuitry 32, may determine that the subject is fatigued, while the failure of the fatigue information to satisfy any of the predetermined combinations of fatigue information may cause the system, such as the processing circuitry, to determine that the subject is not fatigued or at least not sufficiently fatigued to merit the determination of a fatigue mitigation strategy such that the system, such as a processing circuitry, continues to monitor fatigue information associated with the subject in order to determine if the subject becomes fatigued in the future.

In an instance in which the subject is determined to be fatigued, the system 30, such as the processing circuitry 32, may determine an estimated effectiveness of each of a plurality of fatigue mitigation strategies based upon the fatigue information for the subject and one or more constraints and characteristics of a respective fatigue mitigation strategy. See block 20 of FIG. 1. In this regard, the system 30, such as the memory 34, may maintain a plurality of characteristics, limits and constraints associated with each fatigue mitigation strategy. In addition, the system 30, such as the memory 34, of one embodiment may include information regarding the expected time until a respective mitigation strategy is felt to be effective, the effective duration of the effectiveness of a respective mitigation strategy and the possible side effects of a fatigue mitigation strategy.

Figure 3:
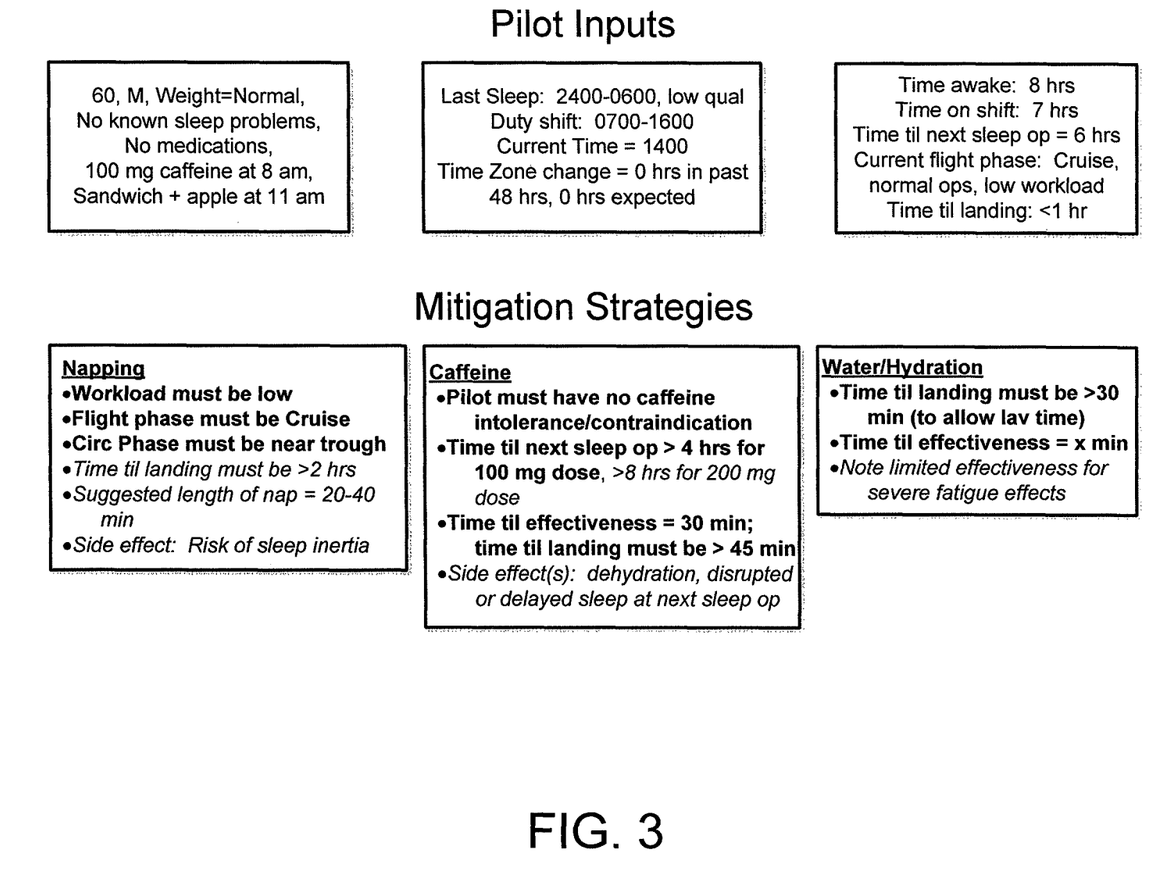
FIG. 3 is an illustration of fatigue information for a subject and the relevance of the fatigue information to each of a plurality of fatigue mitigation strategies.

In this regard, the system 30, such as a processing circuitry 32, may determine which ones of the fatigue information satisfy or otherwise are consistent with characteristics of each respective mitigation strategy and which ones of the fatigue information are inconsistent with a respective mitigation strategy as a result of exceeding a predefined limit or failing to satisfy a constraint associated with a respective mitigation strategy. In addition, the system 30, such as the processing circuitry 32, may determine from the fatigue information whether the expected time until a respective fatigue mitigation strategy is felt to be effective, the expected duration of the effectiveness of the respective fatigue mitigation strategy and the possible side effects of the fatigue mitigation strategy are consistent with the respective mitigation strategy and the circumstances under which the subject is currently operating. By way of example, FIG. 3 illustrates an example in which the fatigue information for a subject has been provided and a system 30, such as the processing circuitry 32, has determined the relationship of the fatigue information to the characteristics, constraints and other information associated with each respective mitigation strategy. In this regard, the characteristics of each respective mitigation strategy, e.g., napping, ingesting caffeine and ingesting water or other forms of hydration, that are satisfied by the fatigue information are shown in bold, while those characteristics of the respective mitigation strategies that are inconsistent or otherwise do not match with the fatigue information are shown in italics.

The system 30, such as the processing circuitry 32, of one embodiment may determine the number of characteristics of each fatigue mitigation strategy that are satisfied by the fatigue information and may take into account any of those characteristics that are weighted. For example, the system 30, such as the processing circuitry 32, may determine a score representative of the estimated effectiveness for each fatigue mitigation strategy that is attributable to the number of characteristics of a respective fatigue mitigation strategy that are satisfied by the fatigue information for the subject, as adjusted by the weighting of the fatigue information that matches with or satisfies the characteristics of a respective fatigue mitigation strategy. For example, the score may be greater as the number of characteristics of a respective fatigue mitigation strategy that are satisfied by the fatigue information for the subject increase and/or as the fatigue information that matches with or satisfies the characteristics of a respective fatigue mitigation strategy is more greatly weighted. Conversely, the score may be lower as the number of characteristics of a respective fatigue mitigation strategy that are satisfied by the fatigue information for the subject decrease and/or as the fatigue information that matches with or satisfies the characteristics of a respective fatigue mitigation strategy is more lightly weighted, if at all.

In regards to determining the estimated effectiveness of each of a plurality of fatigue mitigation strategies, the system 30, such as the processing circuitry 32, may be configured to exclude one or more fatigue mitigation strategies that are in conflict with highly weighted fatigue information, such as fatigue information having a weight that exceeds a predefined threshold. In this regard, the system 30, such as the processing circuitry 32, may ensure that a fatigue mitigation strategy is not recommended to the subject in an instance in which a characteristic of the fatigue mitigation strategy conflicts with fatigue information associated with the subject that is considered to be of importance as indicated by its relatively high weighting.

Figure 4:
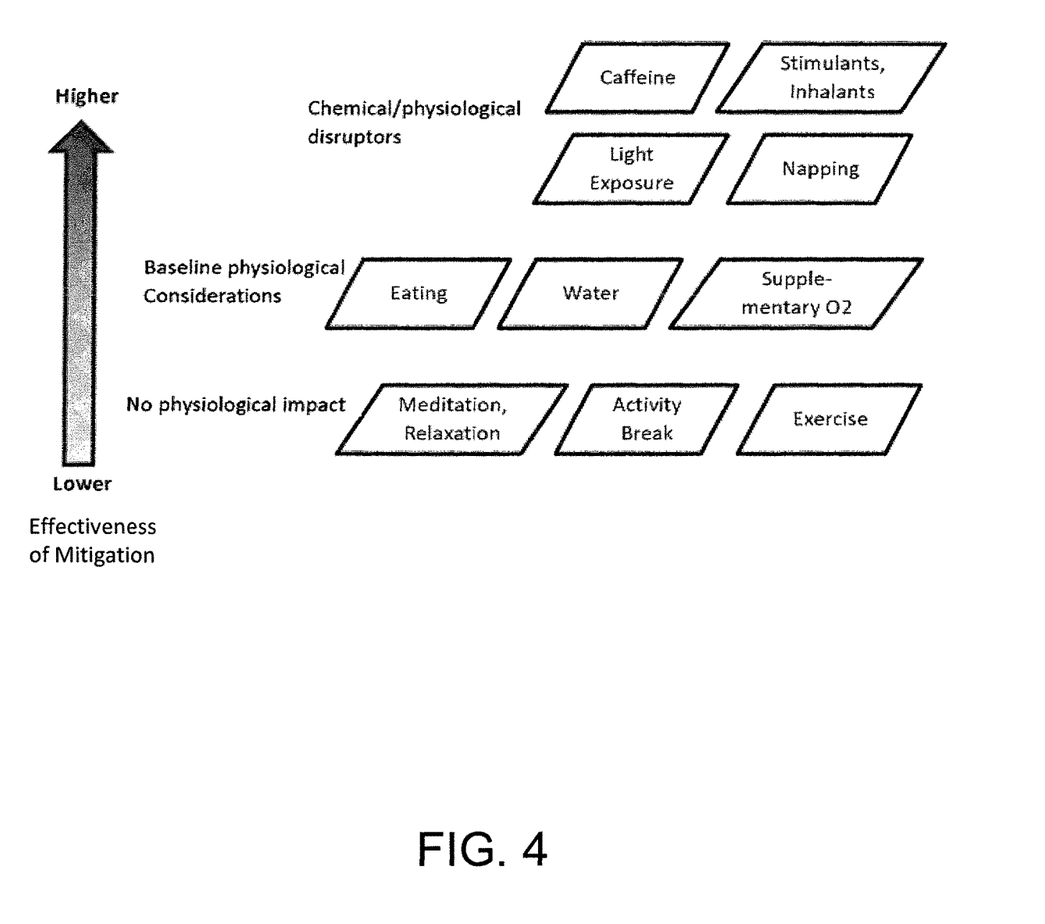
FIG. 4 is an illustration of an ordering of a plurality of fatigue mitigation strategies based upon their estimated effectiveness in accordance with an example embodiment of the present disclosure.

The system 30, such as the processing circuitry 32, of one embodiment may also be configured to identify at least one fatigue mitigation strategy to address the fatigue of a subject. See block 22 of FIG. 1. In one embodiment, for example, the system 30, such as the processing circuitry 32, may identify one or more fatigue mitigation strategies that may address the subject's fatigue in different degrees. In this embodiment, the system 30, such as the processing circuitry 32, may be configured to order the plurality of fatigue mitigation strategies based upon the estimated effectiveness of each respective fatigue mitigation strategy, such as based upon the scores representative of the estimated effectiveness of the fatigue mitigation strategies. By way of example, FIG. 4 is a descriptive illustration of the hierarchy of mitigation effectiveness and the variety of fatigue mitigation strategies under consideration by the system 30. In the illustration of FIG. 4, the various fatigue mitigation strategies being ordered from those fatigue mitigation strategies that have little or no physiological impact, such as meditation, relaxation, an activity break, or exercise, to the more highly effective fatigue mitigation strategies, such as those involving chemical or physiological disruptors, such as caffeine, stimulants, inhalants, light exposure and napping. As such, the system 30 may determine which one or more of the fatigue mitigation strategies to be recommended in order to reduce the fatigue and the potentially deleterious effects caused by the fatigue.

In order to facilitate the selection by the subject of one or more of the recommended fatigue mitigation strategies, the system 30, such as the processing circuitry 32, may be configured to cause information to be presented, such as upon the user interface 36, regarding the fatigue mitigation strategies including the relative effectiveness level, e.g., high or low, the manner of implementing the different fatigue mitigation strategies and any other associated information, such as information regarding the time for the respective fatigue mitigation strategy to become effective, the duration of the effectiveness of the fatigue mitigation strategy and side effects of the fatigue mitigation strategy. See, for example, FIG. 5. Based upon the information regarding the fatigue mitigation strategies, the subject may then select one or more of the fatigue mitigation strategies for implementation.

Figure 5:
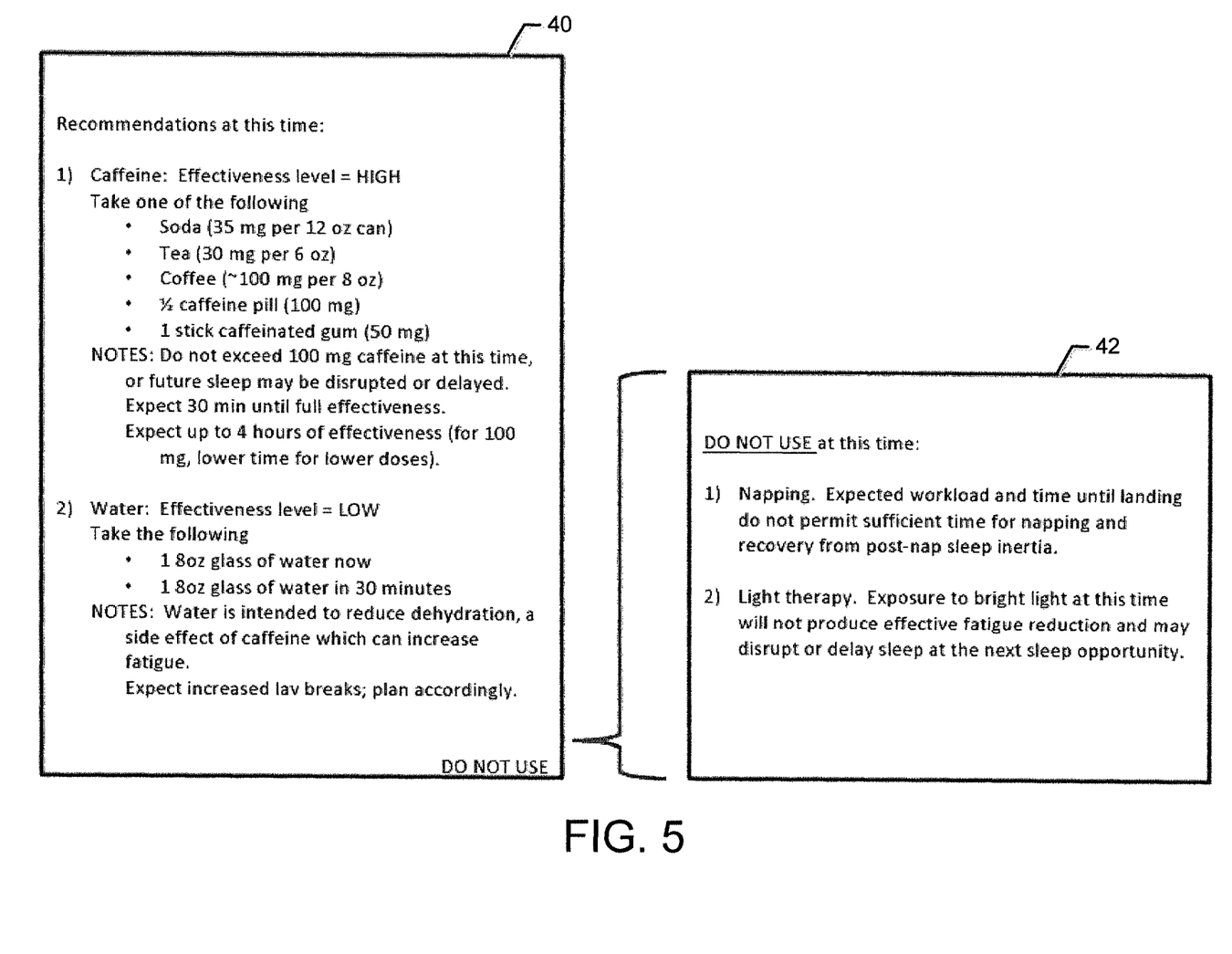
FIG. 5 is an illustration of a plurality of fatigue mitigation strategies that may be utilized to address fatigue in a subject and a plurality of fatigue mitigation strategies that are not recommend for the subject in accordance with an example embodiment of the present disclosure.

In one embodiment, the system 30, such as the processing circuitry 32, is also configured to identify one or more fatigue mitigation strategies that are not recommended for the subject. See block 24 of FIG. 1. For example, the fatigue mitigation strategies that are not recommended for the subject may have been excluded during the determination of the estimated effectiveness of the fatigue mitigation strategies for having characteristics that are in conflict with highly weighted fatigue information. As shown in FIG. 5, for example, the system 30, such as the processing circuitry 32, may cause one or more fatigue mitigation strategies that are not recommended for the subject to be presented, such as upon the user interface 36. In the illustrated embodiment, the fatigue mitigation strategies that are not recommended for the subject are not only identified, but information regarding the reasons as to why the respective fatigue mitigation strategies are not recommended are provided, thereby further discouraging the subject from implementing one or more of the fatigue mitigation strategies that are not recommended.

By providing information regarding one or more fatigue mitigation strategies that are recommended for implementation by the subject and, in some embodiments, information regarding one or more fatigue mitigation strategies are not recommended for the subject, the subject may receive a tailored assessment based upon individual information of the subject and the circumstances that currently confront the subject such that implementation of one or more of the recommended fatigue mitigation strategies has a high likelihood of reducing the fatigue of the subject. As such, the deleterious effects that may otherwise occur as a result of fatigue may be reduced or eliminated, while avoiding implementation by a subject of fatigue mitigation strategies that are based on generic information but that may not be helpful for the specific subject in the current circumstances and, in some instances, that may actually be counter-productive.

FIG. 1 illustrates a block diagram of an example apparatus, method and/or computer program product according to one embodiment. It will be understood that each block of the block diagram, and/or combinations of blocks in the block diagram, can be implemented by various means. Means for implementing the blocks of the block diagram, combinations of the blocks in the block diagram, or other functionality of example embodiments described herein may include hardware, and/or a computer program product including a computer-readable storage medium (as opposed to a computer-readable transmission medium which describes a propagating signal) having one or more computer program code instructions, program instructions or executable computer-readable program code instructions stored therein. In this regard, program code instructions for carrying out the operations and functions of the blocks of FIG. 1 and otherwise described herein may be stored in the memory device of an example apparatus, and executed by the processing circuitry 32. As will be appreciated, any such program code instructions may be loaded onto a computer or other programmable apparatus (e.g., processing circuitry, memory device 34 or the like) from a computer-readable storage medium to produce a particular machine, such that the particular machine becomes a means for implementing the functions specified in the block diagram's blocks.

These program code instructions may also be stored in a computer-readable storage medium that can direct a computer, processing circuitry or other programmable apparatus to function in a particular manner to thereby generate a particular machine or particular article of manufacture. The instructions stored in the computer-readable storage medium may produce an article of manufacture, where the article of manufacture becomes a means for implementing the functions specified in the block diagram's blocks. The program code instructions may be retrieved from a computer-readable storage medium and loaded into a computer, processing circuitry or other programmable apparatus to configure the computer, processing circuitry or other programmable apparatus to execute operations to be performed on or by the computer, processing circuitry or other programmable apparatus. Retrieval, loading and execution of the program code instructions may be performed sequentially such that one instruction is retrieved, loaded and executed at a time. In some example embodiments, retrieval, loading and/or execution may be performed in parallel such that multiple instructions are retrieved, loaded and/or executed together. Execution of the program code instructions may produce a computer-implemented process such that the instructions executed by the computer, processing circuitry or other programmable apparatus provide operations for implementing the functions specified in the block diagram's blocks.

Accordingly, execution of instructions associated with the operations of the blocks of the block diagram by processing circuitry 32, or storage of instructions associated with the blocks of the block diagram in a computer-readable storage medium, supports combinations of operations for performing the specified functions. It will also be understood that one or more blocks of the block diagram, and combinations of blocks in the block diagram, may be implemented by special purpose hardware-based computer systems and/or processing circuitry which perform the specified functions, or combinations of special purpose hardware and program code instructions.

Many modifications and other embodiments set forth herein will come to mind to one skilled in the art to which these embodiments pertain having the benefit of the teachings presented in the foregoing descriptions and the associated drawings. Therefore, it is to be understood that the embodiments are not to be limited to the specific ones disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions other than those explicitly described above are also contemplated as may be set forth in some of the appended claims. Although specific terms are employed herein, they are used in a generic and descriptive sense only and not for purposes of limitation.

That which is claimed:

1. A method for automated assessment of a plurality of fatigue mitigation strategies, the method comprising:
   receiving fatigue information for a human subject;
   determining if the subject is fatigued;

weighting the fatigue information based upon a value of a respective type of parameter included within the fatigue information to a determination of an estimated effectiveness of the plurality of fatigue mitigation strategies such that fatigue information that includes different types of parameters are weighted differently by processing circuitry with fatigue information that is more valuable to the determination of the estimated effectiveness of the plurality of fatigue mitigation strategies having a greater weight applied by the processing circuitry than fatigue information that is less valuable to the determination of the estimated effectiveness of the plurality of fatigue mitigation strategies, wherein a respective type of parameter has a value to the determination of the estimated effectiveness of the plurality of fatigue mitigation strategies that is based upon gender, age and strength of effect on fatigue represented by the fatigue information with fatigue information associated with gender being of more value than fatigue information associated with age and fatigue information representative of a stronger effect on fatigue being of more value than fatigue information representative of a weaker effect on fatigue;

in an instance in which the subject is fatigued, determining, with the processing circuitry, the estimated effectiveness of each of the plurality of fatigue mitigation strategies based upon a relationship between the fatigue information for the subject that has been received and one or more constraints and characteristics of a respective fatigue mitigation strategy that are stored by a memory and further based upon the weighting of the fatigue information, wherein determining the estimated effectiveness of each of the plurality of fatigue mitigation strategies comprises determining a score based on the plurality of characteristics of a respective fatigue mitigation strategy including a count of a number of the plurality of characteristics of the respective fatigue mitigation strategy that are satisfied by the fatigue information with the score being adjusted based upon the weighting of the fatigue information that matches with or satisfies the characteristics of the respective fatigue mitigation strategy, wherein determining the score comprises determining the score, with the processing circuitry, to be greater as the number of the plurality of characteristics of the respective fatigue mitigation strategy that are satisfied by the fatigue information for the subject increase and to be greater as the fatigue information that matches with or satisfies the characteristics of the respective fatigue mitigation strategy has a greater weight, and wherein determining the score further comprises determining the score, with the processing circuitry, to be lower as the number of the plurality of characteristics of the respective fatigue mitigation strategy that are satisfied by the fatigue information for the subject decrease and to be lower as the fatigue information that matches with or satisfies the characteristics of the respective fatigue mitigation strategy has a lighter weight; and identifying at least one of the plurality of different fatigue mitigation strategies to address fatigue of the subject, wherein the plurality of different fatigue mitigation strategies include fatigue mitigation strategies in which the subject performs different types of actions which cause different physiological or chemical impacts upon the subject including two or more different members of the group consisting of an inhalant, light exposure, napping, eating, supplementary oxygen, meditation, and exercise.

2. A method according to claim 1 wherein receiving fatigue information for the subject comprises receiving state information relating to fatigue of the subject or efficacy of one or more of the mitigation strategies.

3. A method according to claim 1 wherein receiving fatigue information for the subject comprises receiving information from one or more fatigue detection devices regarding one or more fatigue effects of the subject.

4. A method according to claim 3 further comprising determining a strength of the one or more fatigue effects.

5. A method according to claim 1 wherein determining the estimated effectiveness of each of the plurality of fatigue mitigation strategies comprises excluding one or more fatigue mitigation strategies that are in conflict with highly weighted fatigue information.

6. A method according to claim 1 wherein determining the estimated effectiveness of each of the plurality of fatigue mitigation strategies comprises determining the estimated effectiveness of each of the plurality of fatigue mitigation strategies based upon at least one of a time to become effective, a duration of the effectiveness or a side effect.

7. A method according to claim 1 wherein identifying at least one fatigue mitigation strategy comprises ordering the plurality of fatigue mitigation strategies based upon the estimated effectiveness.

8. A method according to claim 1 further comprising identifying at least one fatigue mitigation strategy that is not recommended for the subject.

9. A system for automated assessment of a plurality of fatigue mitigation strategies, the system comprising processing circuitry configured to:

receive fatigue information for a human subject;

determine if the subject is fatigued;

weight the fatigue information based upon a value of a respective type of parameter included within the fatigue information to a determination of an estimated effectiveness of the plurality of fatigue mitigation strategies, wherein the processing circuitry is configured such that fatigue information that includes different types of parameters are weighted differently with fatigue information that is more valuable to the determination of the estimated effectiveness of the plurality of fatigue mitigation strategies having a greater weight applied by the processing circuitry than fatigue information that is less valuable to the determination of the estimated effectiveness of the plurality of fatigue mitigation strategies, wherein a respective type of parameter has a value to the determination of the estimated effectiveness of the plurality of fatigue mitigation strategies that is based upon gender, age and strength of effect on fatigue represented by the fatigue information with fatigue information associated with gender being of more value than fatigue information associated with age and fatigue information representative of a stronger effect on fatigue being of more value than fatigue information representative of a weaker effect on fatigue;

in an instance in which the subject is fatigued, determine the estimated effectiveness of each of the plurality of fatigue mitigation strategies based upon a relationship between the fatigue information for the subject that has been received and one or more constraints and characteristics of a respective fatigue mitigation strategy that are stored by a memory and further based upon the weighting of the fatigue information, wherein the processing circuitry is configured to determine the estimated effectiveness of each of the plurality of fatigue mitigation strategies by determining a score based on the plurality of characteristics of a respective fatigue mitigation strategy including a count of a number of the plurality of characteristics of the respective fatigue mitigation strategy that are satisfied by the fatigue information with the score being adjusted based upon the weighting of the fatigue information that matches with or satisfies the characteristics of the respective fatigue mitigation strategy, wherein the processing circuitry is configured to determine the score to be greater as the number of the plurality of characteristics of the respective fatigue mitigation strategy that are satisfied by the fatigue information for the subject increase and to be greater as the fatigue information that matches with or satisfies the characteristics of the respective fatigue mitigation strategy has a greater weight, and wherein the processing circuitry is configured to determine the score to be lower as the number of the plurality of characteristics of the respective fatigue mitigation strategy that are satisfied by the fatigue information for the subject decrease and to be lower as the fatigue information that matches with or satisfies the characteristics of the respective fatigue mitigation strategy has a lighter weight; and identify at least one of the plurality of different fatigue mitigation strategies to address fatigue of the subject, wherein the plurality of different fatigue mitigation strategies include fatigue mitigation strategies in which the subject performs different types of actions which cause different physiological or chemical impacts upon the subject including two or more different members of the group consisting of an inhalant, eating, supplementary oxygen, meditation, and exercise.

10. A system according to claim 9 wherein the processing circuitry is configured to receive fatigue information for the subject by receiving state information relating to fatigue of the subject or efficacy of one or more of the mitigation strategies.

11. A system according to claim 9 wherein the processing circuitry is configured to receive fatigue information for the subject by receiving information from one or more fatigue detection devices regarding one or more fatigue effects of the subject.

12. A system according to claim 11 wherein the processing circuitry is further configured to determine a strength of the one or more fatigue effects.

13. A system according to claim 9 wherein the processing circuitry is configured to determine the estimated effectiveness of each of the plurality of fatigue mitigation strategies by excluding one or more fatigue mitigation strategies that are in conflict with highly weighted fatigue information.

14. A system according to claim 9 wherein the processing circuitry is configured to determine the estimated effectiveness of each of the plurality of fatigue mitigation strategies by determining the estimated effectiveness of each of the plurality of fatigue mitigation strategies based upon at least one of a time to become effective, a duration of the effectiveness or a side effect.

15. A system according to claim 9 wherein the processing circuitry is configured to identify at least one fatigue mitigation strategy by ordering the plurality of fatigue mitigation strategies based upon the estimated effectiveness.

16. A system according to claim 9 wherein the processing circuitry is further configured to identify at least one fatigue mitigation strategy that is not recommended for the subject.

17. A computer program product configured to automatically assess a plurality of fatigue mitigation strategies, the computer program product comprising a non-transitory computer-readable storage medium having computer-readable program code stored therein that in response to execution by processing circuitry cause an apparatus to at least:

receive fatigue information for a human subject;

determine if the subject is fatigued;

weight the fatigue information based upon a value of a respective type of parameter included within the fatigue information to a determination of an estimated effectiveness of the plurality of fatigue mitigation strategies, wherein the computer-readable program code, in response to execution by the processing circuitry, causes the apparatus to weight fatigue information that includes different types of parameters differently with fatigue information that is more valuable to the determination of the estimated effectiveness of the plurality of fatigue mitigation strategies having a greater weight applied than fatigue information that is less valuable to the determination of the estimated effectiveness of the plurality of fatigue mitigation strategies, wherein a respective type of parameter has a value to the determination of the estimated effectiveness of the plurality of fatigue mitigation strategies that is based upon gender, age and strength of effect on fatigue represented by the fatigue information with fatigue information associated with gender being of more value than fatigue information associated with age and fatigue information representative of a stronger effect on fatigue being of more value than fatigue information representative of a weaker effect on fatigue;

in an instance in which the subject is fatigued, determine the estimated effectiveness of each of the plurality of fatigue mitigation strategies based upon a relationship between the fatigue information for the subject that has been received and one or more constraints and characteristics of a respective fatigue mitigation strategy that are stored by the storage medium and further based upon the weighting of the fatigue information, wherein the computer-readable program code for determining the estimated effectiveness of each of the plurality of fatigue mitigation strategies comprises computer-readable program code for determining a score based on the plurality of characteristics of a respective fatigue mitigation strategy including a count of a number of the plurality of characteristics of the respective fatigue mitigation strategy that are satisfied by the fatigue information with the score being adjusted based upon the weighting of the fatigue information that matches with or satisfies the characteristics of the respective fatigue mitigation strategy, wherein the computer-readable program code for determining the score comprises computer-readable program code for determining the score to be greater as the number of the plurality of characteristics of the respective fatigue mitigation strategy that are satisfied by the fatigue information for the subject increase and to be greater as the fatigue information that matches with or satisfies the characteristics of the respective fatigue mitigation strategy has a greater weight, and wherein the computer-readable program code for determining the score further comprises computer-readable program code for determining the score to be lower as the number of the plurality of characteristics of the respective fatigue mitigation strategy that are satisfied by the fatigue information for the subject decrease and to be lower as the fatigue information that matches with or satisfies the characteristics of the respective fatigue mitigation strategy has a lighter weight; and identify at least one of the plurality of different fatigue mitigation strategies to address fatigue of the subject, wherein the plurality of different fatigue mitigation strategies include fatigue mitigation strategies in which the subject performs different types of actions which cause different physiological or chemical impacts upon the subject including two or more different members of the group consisting of an inhalant, eating, supplementary oxygen, meditation, and exercise.

18. A computer program product according to claim 17 wherein the computer-readable program code, in response to execution by the processing circuitry, further causes the apparatus to identify at least one fatigue mitigation strategy that is not recommended for the subject.

19. A method according to claim 1 further comprising maintaining a plurality of characteristics and constraints associated with the plurality of fatigue mitigation strategies in memory.

20. A system according to claim 9 further comprising a memory configured to maintain a plurality of characteristics and constraints associated with the plurality of fatigue mitigation strategies.

* * * * *